United States Patent
Lavi (10) Patent No.: US 9,289,770 B2
(45) Date of Patent: Mar. 22, 2016

(54) RFID—SPECIMEN TRANSPORT PUCK PROCESS FEATURES AND PROCESS METHOD TO EFFICIENTLY WAND, RACK, TRANSPORT, TRACK SPECIMENS IN THE LABORATORY

(75) Inventor: Lear Sirous Lavi, Dana Point, CA (US)

(73) Assignee: LEAR LAVI, Laguna Niguel, CA (US)

(*) Notice: Subject to any disclaimer, the term of this patent is extended or adjusted under 35 U.S.C. 154(b) by 47 days.

(21) Appl. No.: 12/714,442

(22) Filed: Feb. 27, 2010

(65) Prior Publication Data
US 2013/0027185 A1   Jan. 31, 2013

(51) Int. Cl.
*G06K 7/01* (2006.01)
*B01L 9/06* (2006.01)
*B01L 3/00* (2006.01)
*G01N 35/04* (2006.01)

(52) U.S. Cl.
CPC ... *B01L 9/06* (2013.01); *B01L 3/54* (2013.01); *G01N 35/04* (2013.01); *B01L 3/5453* (2013.01); *B01L 2300/022* (2013.01)

(58) Field of Classification Search
CPC ............ G01N 15/0205; G01N 35/00732; G01N 35/04; G01N 2035/00782; G01N 2035/00801; G06K 7/01
USPC ......... 340/10.1, 10.2, 10.3, 10.4, 10.5, 686.1; 235/494, 492, 375, 454; 422/63, 67, 422/100
See application file for complete search history.

(56) References Cited

U.S. PATENT DOCUMENTS

| | | | |
|---|---|---|---|
| 2009/0026907 A1* | 1/2009 | Davidowitz et al. | 312/407 |
| 2010/0188244 A1* | 7/2010 | Sattler et al. | 340/686.1 |
| 2011/0095864 A1* | 4/2011 | Trueeb et al. | 340/10.1 |
| 2011/0118626 A1* | 5/2011 | Ragin et al. | 600/573 |

* cited by examiner

Primary Examiner — Nabil Syed

(57) ABSTRACT

This invention is for the process method of an RFID Specimen Transport puck that can be used in the process of performing overall efficient receiving of specimen identifying information, racking, transporting and tracking of specimens throughout the entire lab. This puck design process can be used on a conveyor system, contains an RFID chip, can be used to wand specimens for tracking, can be used to rack specimens, can be used to transport specimens to laboratory areas and instruments, can be used to track specimen, is made of plastics, is small, has the ability to hold various tubes sizes, that has few pieces to assemble, that is low in cost, can be held in a rack carrying tray. By having all these process features in the one puck design, this 'puck' can be used in high volume and can be used though out the entire laboratory.

20 Claims, 9 Drawing Sheets

FIG. 1
RFID Puck Holding Specimen Tube With Barcode

Specimen Tube Barcode label

Specimen transport puck with RFID for Information Binding

Specimen Transport Puck Slot for Holding Rack

Re-Write RFID chip at bottom of specimen transport puck

FIG. 2
RFID Chip In Bottom of Specimen Transport Puck

RFID Re-Write Chip located at bottom of Specimen Transport Puck. Holds the information from the barcode on the specimen tube

FIG. 3/1
Specimen Transport Puck Sleeve and Rack System 0.85 inches

Racking Sleeves

3X12 Rack/Puck Configuration (36)

FIG. 3/2
5X12 Rack/Puck Configuration (60)

6X12 Rack/Puck Configuration (72)

FIG. 3/3
8X12 Rack/Puck Configuration (96)

FIG. 4
RFID Specimen Transport Puck – All Plastic Injection Molded

Specimen Transport Puck is all Plastic Injection Molded. Has Plastic holders that extend from the fingers that surround the specimen Plastic holders extend from fingers and allow puck to hold any size specimen tube Puck fingers (3 or 4) surround the specimen tube and are open to all barcode read on tube RFID Re-Write Chip located at bottom of Specimen Transport Puck. Holds the information from the barcode on the specimen tube

FIG. 5/1
RFID Specimen Transport Puck on Continuous Sorting System Conveyor – Sort/Wand into Sort Trays

FIG. 5/2

FIG. 6
RFID Specimen Transport Puck – Designed for Minimum Footprint / Area / Space 0.85 Inches diameter = 0.55 square inch area per puck

FIG. 7
RFID Specimen Transport Puck – 3 or 4 Fingers Allow for Open Areas Around the Specimen Tube to Read Barcode

Fingers surrounding Tube with open areas to allow reading of barcode on tube

Plastic holders extend to allow holding all sizes of specimen tubes

RFID—SPECIMEN TRANSPORT PUCK PROCESS FEATURES AND PROCESS METHOD TO EFFICIENTLY WAND, RACK, TRANSPORT, TRACK SPECIMENS IN THE LABORATORY

FIELD OF THE INVENTION

The present invention relates generally to the process of using an RFID Specimen Transport Puck with unique process features for efficient wanding, racking, transporting, and tracking of specimens throughout the entire specimen testing process in a laboratory.

BACKGROUND OF THE INVENTION

The following background is provided to assist in understanding the invention. Specimens (biological material such as blood, urine, tissues) are obtained from patients and routinely placed in tubes, vials or other collection apparatus and sent to testing laboratories to obtain test results that are reported back to the patient generally through a physician for medical decision making for a patient.

Larger specimen testing laboratories receive a variety of specimens in a variety of types of test tubes (or vials) in a variety of test tube sizes (or vial sizes). These laboratories generally have a specimen processing department that get the specimens ready for the laboratory testing areas. The specimen processing department generally places the specimen into the lab information system (LIS) by creating a specimen identification number in the LIS and a barcode label with the specimen identification on the specimen tube that is used to track the specimen and report the testing results back to the patient. These laboratories generally have many testing instruments (number and variety) that are located over a large square foot facility. The facility is generally segmented into laboratory departments based on the tests and instruments. It is extremely difficult (if not impossible) to have conveyors moving specimen samples to all the various instruments over the large area of the laboratory departments and facility.

Many specimens need to be sorted into particular testing groups in the specimen processing department (example: test code) and hand carried to the particular instrument group performing the testing in the individual testing departments. The specimens are hand sorted to groups or test codes. This requires many resources to perform the hand sorting.

Once the specimens are hand sorted, they are generally hand wanded (the information related to the tube is obtained from the specimen barcode through a barcode reader and placed in a batch or to a location for tracking) and taken to lab area and particular instrument for testing. (The process of hand wanding specimens from the barcode is very labor intensive and requires many resources to perform this task)

The wanded specimens are generally hand wanded to a rack position (operator hand wands the specimen from the barcode label on the tube through a barcode reader and places the specimen in a particular location on a rack so that the specimen can be located later) for tracking. The racks vary is size based on the volume of tests that are to be performed and the batch size for the instrument performing the test. Many racks only have a few specimens wanded to the rack that is taken to the lab and blank positions remain on the fixed racks that are taken to the departments and instruments. (The hand wanding and racking of specimens is very labor intensive and requires many resources to perform this task)

The racked specimens are then generally transported to the labs and instruments on carts. The carts hold various racks with some racks containing only a few specimens for testing. (The racking of specimens are very inefficient and require many racks that are do not utilize the full rack size. Many racks are delivered to the departments with only a few specimens on the rack. The rack is not utilized efficiently and it occupies a large amount of space in the labs)

Once the specimens are transported to the labs and instruments on carts, the lab operators generally build testing batches from the specimens. The batches generally contain controls (low and/or medium and/or high target standards that are used to verify that the instrument is testing the batch properly) and may contain repeats (specimens that are re-tested) from prior testing batches. The specimens on the testing batches are generally hand wanded to the batch location for tracking and proper reporting of test results. Some specimens are run on instruments that do not need batching as the volume allows for more continuous flow or the instrument wands the specimens as they are tested. In these cases the specimens are sometimes hand wanded in the department to identify the location of the specimen prior to testing for tracking purposes. Tracking is critical for specimens in a laboratory to reduce the likelihood that a specimen will be lost. Lost specimens is a critical metric that all labs track. A lost specimen generally requires that a patient have the specimen re-drawn. For some specimens this is impossible since the specimens are irreplaceable. (The hand wanding of specimens from the barcode label on the specimen tube with a barcode reader in the laboratory prior to testing is extremely labor intensive are requires many laboratory operator resources to perform this task)

Most laboratories have manual specimen processing departments that are described above. In some laboratories that have automated specimen processing areas, sorting is done by robots or other sorting systems. Some of the specimens in test tubes or other container apparatus are sometimes moved on a conveyor using a specimen holding device. His holding device is sometimes called a 'puck'. The 'puck' is generally used to move samples of a specimen type that is going to one specific instrument type for testing.

The 'puck' or other holding device will generally move the specimen sample in the tube to a particular instrument for patient result testing. Laboratory workers place the specimens on the pucks while they move on the conveyor belt. The specimens move on the conveyor to a particular specimen testing instrument where the specimen is used in providing a patient test result.

After the specimen is removed from the tube and used in the testing process, a laboratory worker or robot removes the specimen tube from the 'puck' on the conveyor and the 'puck' generally loops around so that a laboratory worker can reload the now empty 'puck' with a new specimen tube. These puck applications are very limited to only very limited instruments that are performing very limited numbers of patient tests. Sorting is only to a few instruments and the instruments are continuous feed high volume flow instruments that do not have batched specimens for testing. The specimen is generally sorted by the barcode on the tube through a barcode reader station that is placed on the conveyor. The puck is rotated at each sort location and the barcode is read. If the specimen can be tested at the particular instrument, the specimen in the puck is directed to the instrument with a gate on the conveyor. These systems can generally sort only to a few instruments and are very expensive and complex.

'Pucks' generally do not have RFID chips in them used to hold information related to the specimen sample it is carrying. 'Pucks' are generally not used to sort samples by particular testing group or test code. 'Pucks' generally do not form into racks that can be carried to various lab areas and instruments for testing. 'Pucks' are generally not used for high speed and high density sorting (sorting to many different sorting locations that are required for larger or mid sized laboratories that have many different instruments and tests to perform) of specimens. 'Pucks' are generally not small in diameter. 'Pucks' generally have many pieces that are assembled to make them costly to manufacture and produce.

Once the specimen is sorted by the robot or other sorting systems, the process of wanding, racking, transporting, and tracking the specimens is manual and is the same as described above for the non-automated specimen processing department laboratories.

Current design pucks generally do not have RFID chips built into the puck. (RFID-Radio Frequency Identification Device)

Current design pucks are large in size. (Greater than 1 inch in diameter and do not allow for high density sorting)

Current design pucks are limited in the size of specimen tubes they can hold.

Current design pucks have many pieces that are assembled.

Current design pucks are expensive to make.

Current design pucks are not used to form racks.

Currently there is no pucks that are designed that are used to perform high volume sorting of specimens, wand specimens, rack specimens, transport specimens on a rack, and to track specimens throughout the laboratory.

By having a puck that has the process features that can be used on a conveyor system, contains an RFID chip, can read barcode on specimen tubes though open fingers on puck, can be used to wand specimens for tracking, can be used to rack specimens, can be used to transport specimens, can be used to track specimens throughout the entire laboratory, is made of plastics, is small, has the ability to hold various tubes sizes, that has few pieces to assemble, that is low in cost, can be held in a rack carrying tray, these 'pucks' can be used in high volume and perform the overall wanding racking, transporting, and tracking of specimens though out the entire laboratory.

SUMMARY OF THE INVENTION

This invention is for the process feature of an RFID Specimen Transport puck that can be used on a conveyor system.

This invention is for the process feature of an RFID Specimen Transport puck that has RFID (Radio Frequency Identification Device) at the bottom of the puck.

This invention is for the process feature of an RFID Specimen Transport puck that can hold most sized specimen tubes.

This invention is for the process feature of an RFID Specimen Transport puck that can be used to wand specimens to a sorted location.

This invention is for the process feature of an RFID Specimen Transport puck that can be taken from the conveyor and used in racks to transport specimens into different laboratory areas/departments while contained on the rack.

This invention is for the process feature of an RFID Specimen Transport puck that is uniquely processed completely out of plastic with aluminum or other flexible material for holding fingers and allows for low cost plastic injection molding.

This invention is for the process feature of an RFID specimen transport puck that is very small and made of plastic that can hold any size specimen sample tube with barcode label.

This invention is for the process feature of an RFID Specimen Transport puck that allows for barcode reading of specimen while in the puck.

This invention is for the process feature of an RFID Specimen Transport Puck that is also uniquely designed to form into a rack system to track and transport the pucks with the specimen tubes.

This invention is for the process feature of an RFID specimen transport puck that has very few pieces to assemble.

This invention is for the process feature of an RFID Specimen Transport puck is very low in cost to manufacture and assemble.

This invention is for the process feature of an RFID Specimen Transport puck that can be used in Tracking Specimens This invention is for the process method of writing a specimen tracking number and/or test code and/or department and/or specimen temperature requirements to the RFID on the puck that is holding the particular specimen.

This invention is for the process method of wanding specimens using a puck with the design features described.

This invention is for the process method of racking specimens using a puck with the design features described.

This invention is for the process method of transporting racked specimens using a puck with the design features described.

This invention is for the process method of tracking specimens using a puck with the design features described.

DESCRIPTION OF DRAWINGS

1. Plastic RFID specimen transport puck is designed to hold any size specimen test tube. (See Diagram 1)
2. Plastic RFID specimen transport puck is designed to hold an RFID tag that can be reused in the specimen testing process. (See Diagram 2)
3. Plastic RFID specimen transport puck is designed to uniquely form into a rack system to transport the pucks with the specimens. (See Diagram 3)
4. Plastic RFID specimen transport puck is designed out of plastic with plastic or aluminum or other flexible holders that extend from the fingers to hold any size tube. The puck has a slot at the bottom for an RFID re-write chip to be installed. (See Diagram 4)
5. Plastic RFID specimen transport puck is designed to be used on a conveyor system and a puck transport rack system for specimen sorting/wanding/storage and transfer. (See Diagram 5)
6. Plastic RFID specimen transport puck is designed to occupy minimum footprint/area and space. (See Diagram 6)
7. Plastic RFID specimen transport puck is designed with 3 or 4 open fingers to hold various specimen tubes and allow for barcode reading of barcode label to take place through the open fingers area of the puck. (See Diagram 7)

DETAILED DESCRIPTION OF THE INVENTION

This invention is for the process feature of an RFID Specimen Transport puck that can be used on a conveyor system.

Figure 5:
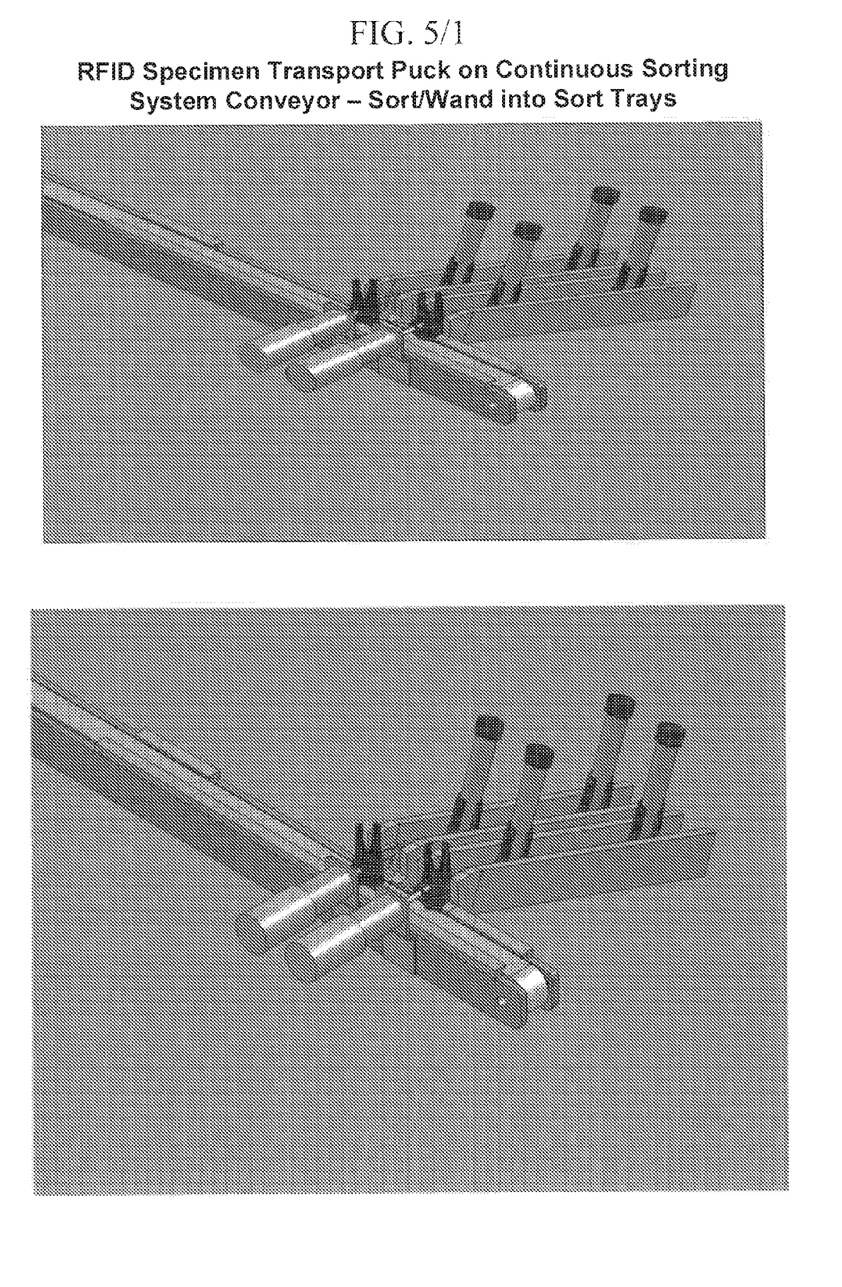

The puck has a double groove slot design at the lower base of the puck. The specimens tubes are placed in the pucks by an operator that logs the specimen into the laboratory information system. The operator then places the puck with the specimen onto the conveyor. The conveyor has a rail that holds the puck down and centered on the conveyor with the groove slot in the puck. The conveyor then can move the specimen continuously to the sorting locations that run off from the conveyor.

This invention is for the process feature of an RFID Specimen Transport puck that has RFID (Radio Frequency Identification Device) at the bottom of the puck.

Figure 2:
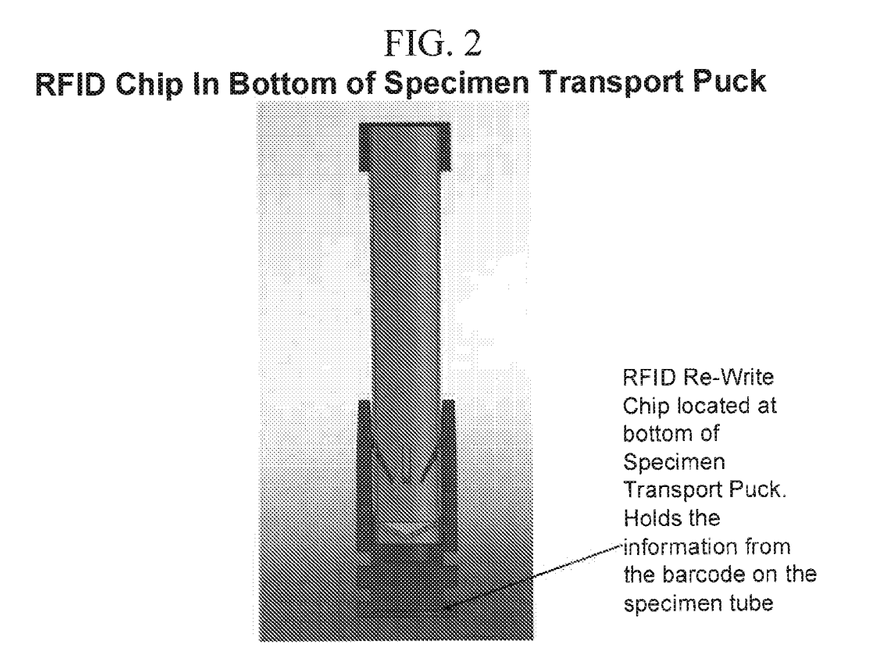

The puck has an RFID chip located at the bottom of the puck. The RFID chip is read/write and has the ability to write information such as the specimen identification, test code, department, temperature (frozen, refrigerated, ambient). The information can be deleted from the RFID and new information can be written to the puck so that it can be reused for sorting, wanding, tracking specimens in the laboratory. The information placed on the RFID is generally from an RFID reader/writer that writes the information after reading the barcode information on the tube. By having the RFID at the bottom of the puck, the information from the tube can be read from the barcode using a barcode reader and then written to the RFID chip through a RFID reader/writer that is beneath the conveyor belt. The barcode information generally contains the specimen identification number and additional information can be written to the chip including the test code that is to be performed on the specimen, the department the specimen is to be taken to for testing, and the temperature the specimen is to be maintained before testing.

This invention is for the process feature of an RFID Specimen Transport puck that can hold most sized specimen tubes.

Figure 1:
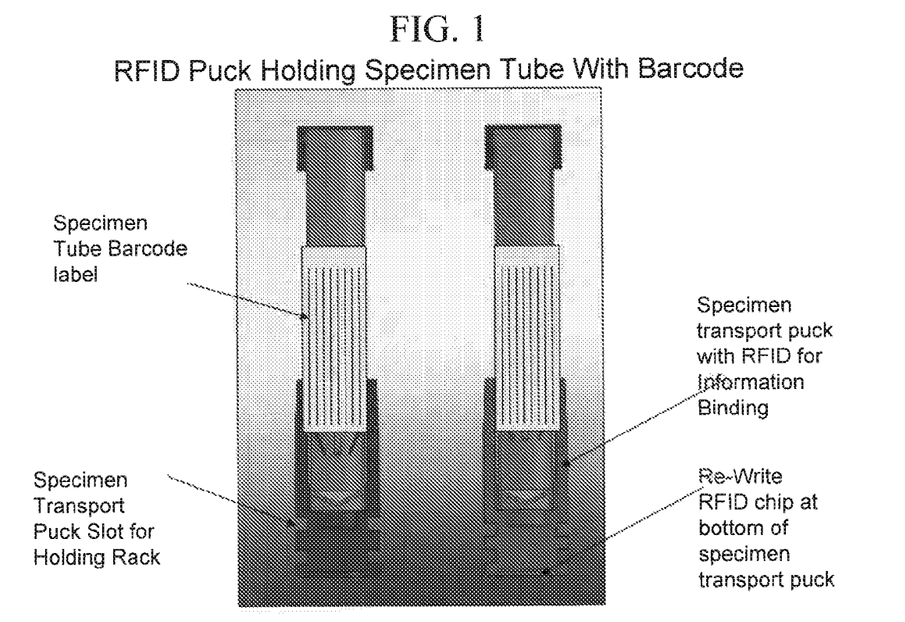
Figure 4:
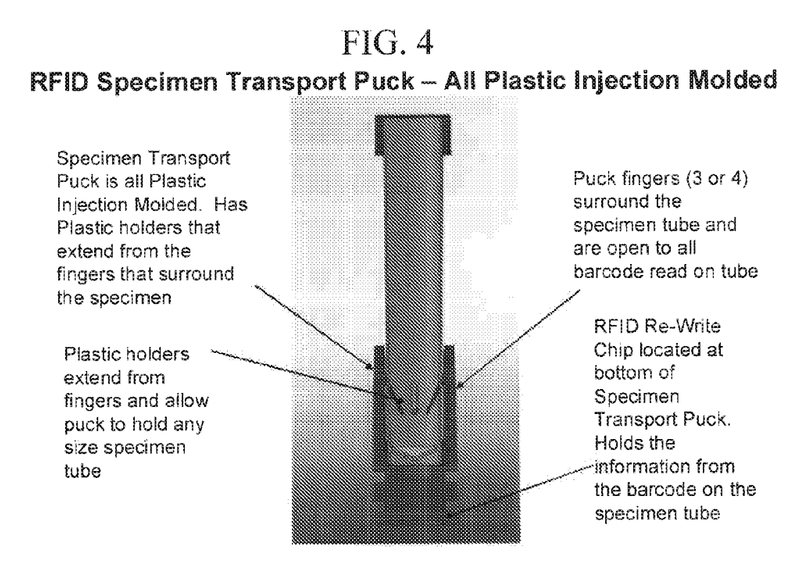

The puck has flexible tube holders that extend from the open fingers that surround the outer edge of the puck. The flexible holders can be made of plastic or aluminum and extend from the top of the fingers and run down and inward toward the center of the puck. As the various sized diameter tubes are placed in the pucks by the operators, the flexible holders spring outward placing a constant pressure onto the various sized diameter tube. Most labs have tubes that have a diameter between 0.25 and 0.50 inches in diameter. The puck can have a diameter that is slightly larger than the diameter of the largest tube.

This invention is for the process feature of an RFID Specimen Transport puck that can be used to wand specimens to a sorted location.

The puck has the RFID chip with the information from the specimen tube it is carrying. (This can occur in a process method that places the information from the barcode on the tube along with other relevant information, to the RFID chip) The puck RFID information can be read by an RFID reader that is beneath the belt as the conveyor moves the puck over the reader. When the puck information (such as the matching test code to the assigned reader) matches the sort location, an actuator can be triggered to push the puck from the conveyor to the designated sort tray. The information now obtained from the RFID reader upon sorting, can now be sent to the laboratory information system with a date and time stamp. This 'Wanded' (reading of RFID information and placing the information into the laboratory information system with a date and time stamp) information now identifies that the specimen is now in a sorted location and available to the lab for testing. The 'wanding' also is used to track the specimen in the lab. The 'wanding' using the RFID from the bottom of the puck that is holding the specimen, completely eliminates the manual wanding step in the for hand wanding the specimens to a rack location before transporting the specimens to the lab areas and instruments. This has tremendous savings in manual labor for this process step.

This invention is for the process feature of an RFID Specimen Transport puck that can be taken from the conveyor and used in racks to transport specimens into different laboratory areas/departments while contained on the rack.

Figure 3:
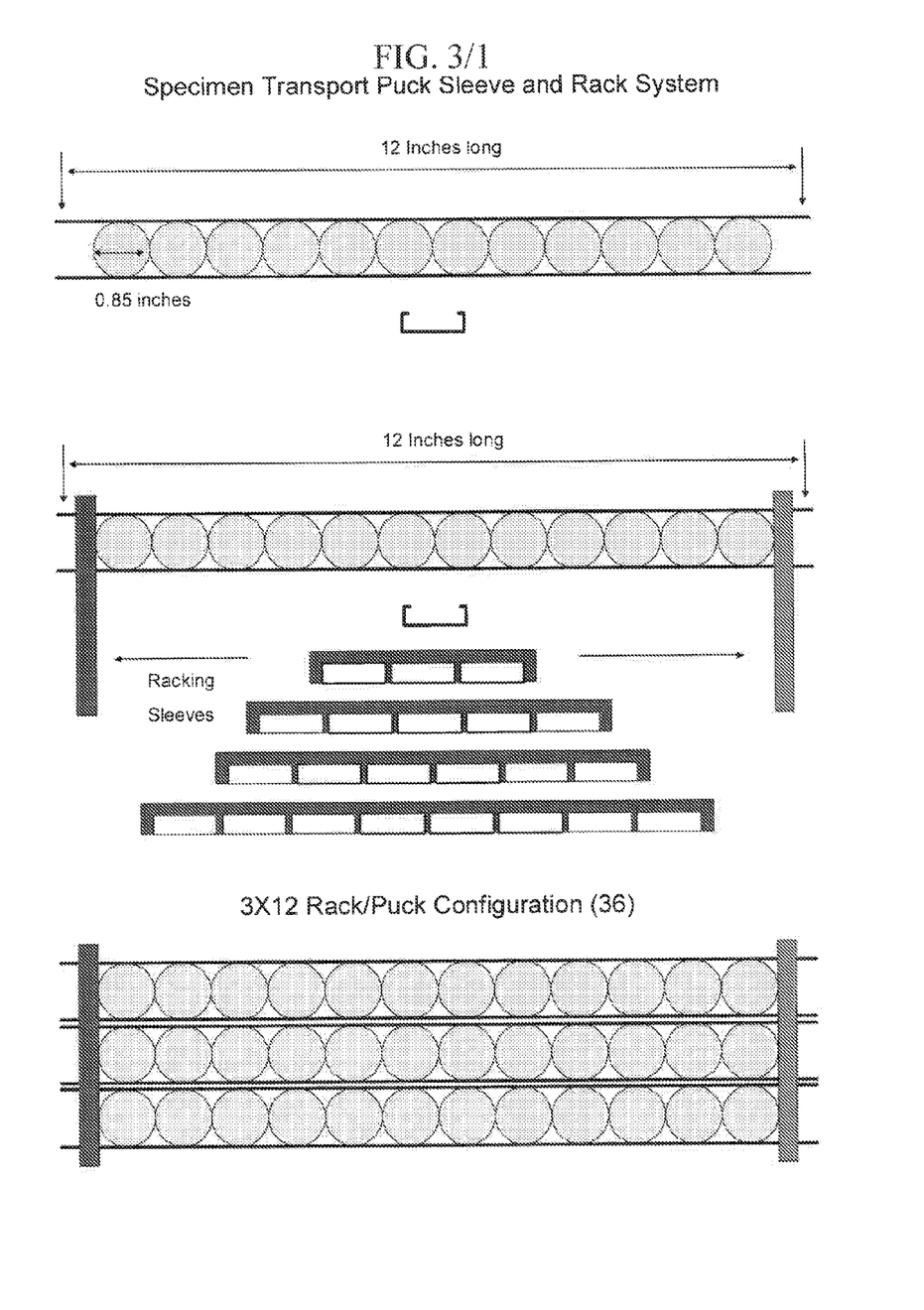

The puck has a double groove design toward the bottom of the puck. The grooves allow the pucks to be held in transport sleeves and to form into racks. The pucks are small in diameter (less than 1.00 inch) and slide onto sleeves. Each sleeve can hold a targeted number of pucks (example 12 pucks on a sleeve, and 3 sleeves forming a rack of 36, 5 sleeves forming a rack of 60, 6 sleeves forming a rack of 72, and 8 sleeves forming a rack of 96) The sleeves form the racks with a holding clip or tray. The racks of pucks holding specimens can then be taken to the labs on a cart directly to the instrument to test the specimens. The racking of specimens without using the RFID Transport Puck with the process features identified in this invention are very inefficient and require many racks that do not utilize the full rack size. Many racks are delivered to the departments with only a few specimens on the rack. The rack is not utilized efficiently and it occupies a large amount of space in the labs. This invention creates racks out of the RFID Specimen Transport Puck. Each puck contains a specimen. There is a one to one correspondence between the puck and specimen. The puck rack process is fully utilized since each puck position contains a specimen. This reduces the space the non-puck specimen racks occupy in the lab. The manual racks with multiple slots for specimens (smallest racks generally have 30 specimen slots) can be very inefficient since low volume tests will be transported on the rack with only a few specimens. This is very costly since the racks are expensive and not fully utilized. The puck rack process is completely efficient with one specimen per puck.

This invention is for the process feature of an RFID Specimen Transport puck that is uniquely processed out of plastic with aluminum or other flexible material for tube holding extensions and allows for low cost plastic injection molding.

The puck is processed out of plastic that can be easily injection molded. The puck has 3 or 4 fingers with open areas around the circumference to allow for barcode reading of the specimen tube while being held in the puck. The lower base of the puck has 1 or 2 grooves that are used to hold the puck on the conveyor and the sleeves for racking. The bottom of the puck has a groove for the RFID chip to be inserted. This one piece plastic design makes the puck low cost. Plastic or Aluminum tube holding extensions can be molded or attached to each finger.

This invention is for the process feature of an RFID specimen transport puck that is very small and made of plastic that can hold any size specimen sample tube with barcode label.

Figure 6:
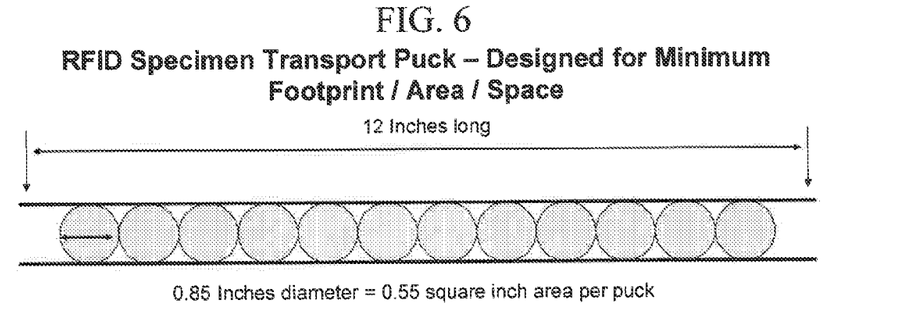

The puck is processed out of plastic that can be easily injection molded. The puck has 3 or 4 fingers with open areas around the circumference to allow for barcode reading of the specimen tube while being held in the puck. The puck is small in diameter (less than 1.00 inch). Plastic or Aluminum tube holding extensions can be molded or attached to each finger. The plastic or aluminum holding extensions are flexible and bend as the various size tubes are inserted into the puck. The plastic or aluminum flexible extensions place constant pressure on the tube.

This invention is for the process feature of an RFID Specimen Transport puck that allows for barcode reading of specimen while in the puck.

Figure 7:
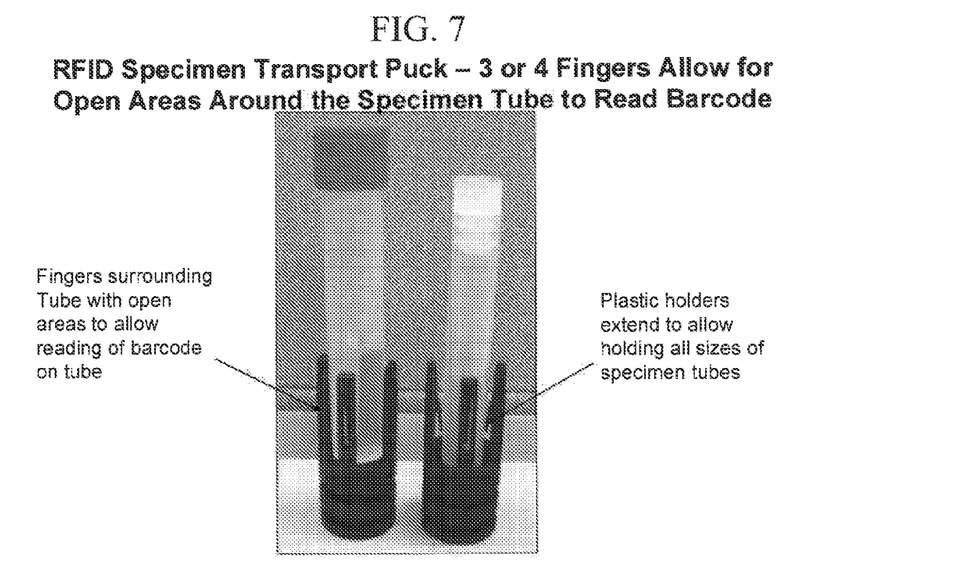

The puck is processed out of plastic that can be easily injection molded. The puck has 3 or 4 fingers with open areas around the circumference to allow for barcode reading of the specimen tube while being held in the puck. The puck can be rotated while a barcode reader reads the barcode information on the specimen tube on the puck. The barcode is read from the open areas between the finders. The barcode information such as specimen identification number (along with other information such as test code, department, temperature) can then be placed into the puck RFID chip.

This invention is for the process feature of an RFID Specimen Transport Puck that is also uniquely designed to form into a rack system to track and transport the pucks with the specimen tubes.

The puck has 1 or 2 grooves designed into the bottom part of the puck. The grooves allow for the specimens to be held and centered on the conveyor. The grooves also allow the pucks to be held in transport sleeves and to form into racks. The pucks are small in diameter (less than 1.00 inch) and slide onto sleeves. Each sleeve can hold a targeted number of pucks (example 12 pucks on a sleeve, and 3 sleeves forming a rack of 36, 5 sleeves forming a rack of 60, 6 sleeves forming a rack of 72, and 8 sleeves forming a rack of 96) The sleeves form the racks with a holding clip or tray. The racks of pucks holding specimens can then be taken to the labs on a cart directly to the instrument to test the specimens. The racking and transporting of specimens without using the RFID Transport Puck with the process features identified in this invention are very inefficient and require many racks that do not utilize the full rack size. Many racks are delivered to the departments with only a few specimens on the rack. The rack is not utilized efficiently and it occupies a large amount of space in the labs. This invention creates racks out of the RFID Specimen Transport Puck. Each puck contains a specimen. There is a one to one correspondence between the puck and specimen. The puck rack process is fully utilized since each puck position contains a specimen. This reduces the space the non-puck specimen racks occupy in the lab. The manual racks with multiple slots for specimens (smallest racks generally have 30 specimen slots) can be very inefficient since low volume tests will be transported on the rack with only a few specimens. This is very costly since the racks are expensive and not fully utilized. The puck rack process is completely efficient with one specimen per puck.

This invention is for the process feature of an RFID specimen transport puck that has very few pieces to assemble.

The puck is processed out of plastic that can be easily injection molded. The puck has 3 or 4 fingers with open areas around the circumference to allow for barcode reading of the specimen tube while being held in the puck. The lower base of the puck has 1 or 2 grooves that are used to hold the puck on the conveyor and the sleeves for racking. The bottom of the puck has a groove for the RFID chip to be inserted. This one piece plastic design makes the puck low cost. Plastic or Aluminum tube holding extensions can be molded or attached to each finger. Only assembly necessary is to insert the RFID chip at the bottom of the puck and to install the 3 or 4 aluminum holding extension to the open fingers around the puck. If plastic is used for the holding extension, the plastic can either be molded as one piece with the base of the puck or attached in a separate assembly process.

This invention is for the process feature of an RFID Specimen Transport puck is very low in cost to manufacture and assemble.

The puck consists of a low cost plastic injection molded piece. A low cost passive RFID chip with read/write repeatability that can be inserted in the bottom of the puck. Low cost aluminum holding extensions can be attached to the fingers. Based on the low cost components and the ability to reuse the puck over and over again in the sorting, wanding, and transporting of specimens throughout the lab, make the puck a very low cost process.

This invention is for the process feature of an RFID Specimen Transport puck that can be used in Tracking Specimens.

The puck has the RFID chip with the information from the specimen tube it is carrying. (This can occur in a process that places the information from the barcode on the tube along with other relevant information, to the RFID chip) The puck RFID information can be read by an RFID reader that is beneath the belt as the conveyor moves the puck over the reader. When the puck information (such as the matching test code to the assigned reader) matches the sort location, an actuator can be triggered to push the puck from the conveyor to the designated sort tray. The information now obtained from the RFID reader upon sorting, can now be sent to the laboratory information system with a date and time stamp. This 'Wanded' (reading of RFID information and placing the information into the laboratory information system with a date and time stamp) information now identifies that the specimen is now in a sorted location and available to the lab for testing. The 'Wanding' also is used to track the specimen in the lab. By having the specimen information in the RFID chip, the racks of pucks that are transported to the departments can be 'wanded' instantly using the RFID with a date and time stamp into the laboratory information system or other tracking system. The racks can be wanded when they are transferred at each step in the movement of specimens in the testing process. The wanding provides the date and time stamp at each station. This wanding of specimens using the RFID along with the RFID antennas in the lab allow for complete tracking of specimens though out the entire laboratory testing process.

This invention is for the process method of writing a specimen tracking number and/or test code and/or department and/or specimen temperature requirements to the RFID on the puck that is holding the particular specimen.

The puck has a passive RFID chip with repeated read/write capabilities. The RFID chip can have information re-written over and over again allowing the puck to be re-useable over and over again. Once an operator places the specimen in a puck and places the puck on the conveyor, the information from the specimen tube it is carrying needs to be placed into the RFID chip on the puck. (This can occur in a process that places the information from the barcode on the tube along with other relevant information, to the RFID chip) The puck holding the specimen tube with the barcode label is rotated on the conveyor and the barcode is read by a barcode reader. The barcode reader is able to read through the open fingers around the puck. Once the barcode information from the tube is read, the barcode information—generally the specimen tracking number—along with other relevant information such as test code, department, temperature can be placed on the RFID chip through an RFID reader/write unit beneath the conveyor belt.

This invention is for the process method of wanding specimens using a puck with the design features described.

The puck has the RFID chip with the information from the specimen tube it is carrying. (This can occur in a binding process that places the information from the barcode on the tube along with other relevant information, to the RFID chip) The puck RFID information can be read by an RFID reader that is beneath the belt as the conveyor moves the puck over the reader. When the puck information (such as the matching test code to the assigned reader) matches the sort location, an actuator can be triggered to push the puck from the conveyor to the designated sort tray. The information now obtained from the RFID reader upon sorting, can now be sent to the laboratory information system with a date and time stamp.

This 'wanded' (reading of RFID information and placing the information into the laboratory information system with a date and time stamp) information now identifies that the specimen is now in a sorted location and available to the lab for testing. The 'Wanding' also is used to track the specimen in the lab. By having the specimen information in the RFID chip, the racks of pucks that are transported to the departments can be 'wanded' instantly using the RFID with a date and time stamp into the laboratory information system or other tracking system. The racks can be wanded when they are transferred at each step in the movement of specimens in the testing process. The wanding provides the date and time stamp at each station. This wanding of specimens using the RFID along with the RFID antennas in the lab allow for complete tracking of specimens though out the entire laboratory testing process. The process of hand wanding specimens is very labor intensive and requires many resources to perform this task) The wanding process using the RFID Transport Puck can be done in seconds by reading the RFID information from the puck rack when placed on a RFID rack reader. This process saves a tremendous amount of resource time to perform wanding throughout the entire laboratory.

This invention is for the process method of racking specimens using a puck with the design features described.

The puck has 1 or 2 grooves designed into the bottom part of the puck. The grooves allow for the specimens to be held and centered on the conveyor. The grooves also allow the pucks to be held in transport sleeves and to form into racks. The pucks are small in diameter (less than 1.00 inch) and slide onto sleeves. Each sleeve can hold a targeted number of pucks (example 12 pucks on a sleeve, and 3 sleeves forming a rack of 36, 5 sleeves forming a rack of 60, 6 sleeves forming a rack of 72, and 8 sleeves forming a rack of 96) The sleeves form the racks with a holding clip or tray. The racks of pucks holding specimens can then be taken to the labs on a cart directly to the instrument to test the specimens.

This invention is for the process method of transporting specimens using a puck with the design features described.

The puck has 1 or 2 grooves designed into the bottom part of the puck. The grooves allow for the specimens to be held and centered on the conveyor. The grooves also allow the pucks to be held in transport sleeves and to form into racks. The pucks are small in diameter (less than 1.00 inch) and slide onto sleeves. Each sleeve can hold a targeted number of pucks (example 12 pucks on a sleeve, and 3 sleeves forming a rack of 36, 5 sleeves forming a rack of 60, 6 sleeves forming a rack of 72, and 8 sleeves forming a rack of 96) The sleeves form the racks with a holding clip or tray. The racks of pucks holding specimens can then be taken to the labs on a cart directly to the instrument to test the specimens.

This invention is for the process method of tracking specimens using a puck with the design features described.

The puck has the RFID chip with the information from the specimen tube it is carrying. (This can occur in a binding process that places the information from the barcode on the tube along with other relevant information, to the RFID chip) The puck RFID information can be read by an RFID reader that is beneath the belt as the conveyor moves the puck over the reader. When the puck information (such as the matching test code to the assigned reader) matches the sort location, an actuator can be triggered to push the puck from the conveyor to the designated sort tray. The information now obtained from the RFID reader upon sorting, can now be sent to the laboratory information system with a date and time stamp. This 'wanded' (reading of RFID information and placing the information into the laboratory information system with a date and time stamp) information now identifies that the specimen is now in a sorted location and available to the lab for testing. The 'Wanding' also is used to track the specimen in the lab. By having the specimen information in the RFID chip, the racks of pucks that are transported to the departments can be 'wanded' instantly using the RFID with a date and time stamp into the laboratory information system or other tracking system. The racks can be wanded when they are transferred at each step in the movement of specimens in the testing process. The wanding provides the date and time stamp at each station. This wanding of specimens using the RFID along with the RFID antennas in the lab allow for complete tracking of specimens though out the entire laboratory testing process The terms and expressions used within this patent have been used in terms of description and are not of limitation and there is no intention in the terms and expressions to exclude any equivalent of the features in the diagrams and descriptions, but recognizes that various modifications are possible within the scope of the invention claimed.

The invention has been described broadly. Each of the narrower features and specifications fall within the generic disclosure also form part of the invention.

What is claimed:

1. A method of improving the receiving of specimen identifying information into a Lab Information System (LIS) or any database information system using an RFID Chip on a Specimen Transport Puck which is a Specimen Tube holding device, wherein:

each individual puck holds an individual specimen tube with barcode information for laboratory testing, and is round, and has RFID chip at the bottom of said each puck wherein the puck has a groove design around the bottom circumference;

using said grooves to convey the puck down on a conveyor line with said specimen top and said RFID chip at the bottom of the puck;

reading the barcode information from the specimen tube and using an RFID reader beneath the conveyor line to write the barcode information to the RFID chip, removing said puck from the conveyor line and using said grooves to hold the puck onto sleeves that also hold the bottom RFID chip of the puck down on said sleeve; wherein said sleeve hold a plurality of pucks and a plurality of sleeves group together to form a rack with a holding clip or tay;

reading the RFID chips of the pucks on said rack with a second RFID reader, to receive specimen information, identify individual position of the specimens in said rack and the location of specimens at various locations throughout the laboratory sending the specimen information, the identified individual position and the location of the specimen into the lab information system or any database information system, with date and time stamp or other relevant locating information, at various locations, when the specimen is sorted on the conveyor from the RFID reader beneath the conveyor on to sleeves when the grouped sleeves forming racks are transported from sorting area, when the grouped sleeves forming racks are received into the individual lab department areas, when the grouped sleeves forming racks are arranged for testing on instrument batches, when the grouped sleeves forming racks are removed from the departments, when the grouped sleeves forming racks are placed into long term storage for possible retrieval of specimen tube for additional testing, or other locations throughout the laboratory wherein this process improvement greatly reduces the manual labor cost over the manual receiving of the barcode information from each specimen using a barcode label on a tube and a barcode reader wherein this greatly improves the efficiency of specimen receiving information into the database information system.

2. A method of racking specimens for transport comprising use of an RFID specimen transport puck which is a Specimen Tube holding device, wherein:

wherein each individual puck holds an individual specimen tube with barcode information for laboratory testing, and is round, and has a RFID chip at the bottom of said each puck wherein the puck has a groove design around the bottom circumference;

using said grooves to convey the puck down on a conveyor line with said specimen tube on top and said RFID chip at the bottom of the puck;

reading the barcode information from the specimen tube and using an RFID reader beneath the conveyor line to write the barcode information to the RFID chip, removing said puck from the conveyor line and using said grooves to hold the puck onto sleeves that also hold the bottom RFID chip of the puck down on said sleeve; wherein said sleeve hold a plurality of pucks and a plurality of sleeves group together to form a rack with a holding clip or tay;

reading the RFID chips of the pucks on said rack with a second RFID reader, to receive specimen information, identify indiviidual position of the specimens in said rack and the location of specimens at various locations throughout the laboratory wherein the RFID specimen transport puck holding sleeves that hold the RFID specimen transport pucks and form a rack wherein this process improvement greatly reduces the manual labor cost and greatly improves the efficiency over manually placing specimens out of the specimen transport pucks and wanding into new racks for transporting.

3. A method of tracking specimens comprising use of an RFID specimen transport puck which is a Specimen Tube holding device, wherein:

each individual puck holds an individual specimen tube with barcode information for laboratory testing, and is round, and has a RFID chip at the bottom of said each puck wherein the puck has a groove design around the bottom circumference;

using said grooves to convey the puck down on a conveyor line with said specimen tube on top and sad RFID chip at the bottom of the puck;

reading the barcode information from the specimen tube and using an RFID reader beneath the conveyor line to write-to the barcode information to the RFID chip, removing said Puck from the conveyor line and using said grooves to hold the puck onto sleeves that also hold the bottom RFID chip of the puck down on said sleeve; wherein said sleeve hold a plurality of pucks and a plurality of sleeves group together to form a rack with a holding clip or tay;

reading the RFID chips of the pucks on said rack with a second RFID reader, to receive specimen information, identity individual position of the specimens in said rack and the location of specimens at various locations throughout the laboratory when the specimen is sorted on the conveyor from RFID readers beneath the conveyor on to sleeve, when the grouped sleeves forming racks are transported from sorting area, when the grouped sleeves forming racks are received into the individual lab department, areas when the grouped sleeves forming racks are arranged for testing on instrument batches, when the grouped sleeves forming racks are removed from the departments, when the grouped sleeves forming racks are placed into long term storage for possible retrieval of specimen tube for additional testing, or other locations throughout the lab, with specific specimen information of the specimen on the RFID specimen transport puck read into the lab information system or any database information system, with date and time stamp or other relevant locating information with RFID reader wherein this process improvement greatly reduces the manual labor cost of manually entering specimen identifying information from barcode scanning into database information systems for tracking or searching for specimens and greatly improves the efficiency of tracking specimens.

4. The method of claim 1 wherein the receiving of specimen identifying information of specimens includes the process of an said RFID Specimen Transport puck that has the process feature to hold variable sized specimen tubes based on flexible holders extending from the upper posts of the RFID specimen transport puck.

5. The method of claim 1 wherein the receiving of specimen identifying information of specimens into the database information system includes the process of said RFID Specimen Transport puck that has said Radio Frequency Identification Device (RFID) chip at the bottom of the RFID specimen transport puck.

6. The method of claim 1 wherein the receiving of specimen identifying information of specimens on the RFID specimen transport puck into the database information system includes the process of said RFID Specimen Transport puck that is used to receive specific specimen information into said database information system as specimens are separated to a sorted location.

7. The method of claim 2 wherein the racking of specimens for transport includes the process of said RFID Specimen Transport puck that can be taken from the conveyor and used on sleeves that are grouped together into racks of any configuration to transport specimens into different laboratory areas/departments while contained on the rack.

8. The method of claim 1 wherein the receiving of specimen information of specific specimens includes the process of said RFID Specimen Transport puck that is uniquely designed completely out of plastic with aluminum or other flexible material for holding posts and allows for low cost plastic injection molding.

9. The method of claim 2 wherein the racking of specimens for transport includes the process of said RFID specimen transport puck that is very small in diameter (less than 1 inch) which allows the RFID specimen transport pucks to form the rack of small size to be transported to the laboratory areas/departments.

10. The method of claim 1 wherein the receiving of specimen identifying information of specimens into said database information system includes the process of said RFID Specimen Transport puck that allows for barcode reading of specimen while in the RFID specimen transport puck.

11. The method of claim 2 wherein the racking of specimens for transport includes the process of said RFID Specimen Transport Puck for a conveyor that is also uniquely designed to come-off from the conveyor onto said sleeves that group together to form said racks to track the pucks with the specimen tubes by reading the RFID chip of pucks on the racks at various locations throughout the lab into a database with date and time stamp to identify location and time of the last location of the specimen.

12. The method of claim 1 wherein the receiving of specimen identifying information of specimens includes the process of said RFID specimen transport puck that has very few pieces to assemble (3 pieces).

13. The method of claim 2 wherein the racking of specimens for transport includes the process of said RFID Specimen Transport puck that is very low in cost to manufacture and assemble.

14. The method of claim 1 wherein the receiving of specimen identifying information of specimens into said database information system includes the process of writing a specimen tracking number and/or test code and/or department and/or specimen temperature requirement to the RFID chip on the puck that is holding the particular specimen.

15. The method of claim 1 wherein the receiving of specimen identifying information of specimens into said database information system includes the process of rotating the specimen from the RFID pucks and receiving the specimen identifying information from the barcode label on the specimen tube into a database information system with a barcode reader.

16. The method of claim 2 wherein the racking of specimens for transport includes the process of racking of specimens while in said RFID specimen transport pucks by sorted groups or test codes for transport to instruments in specified laboratory departments.

17. The method of claim 2 wherein the racking of specimens for transport includes the process of transporting specimens while in said pucks that form racks that are carted and taken to the laboratory departments and instruments for testing.

18. The method of claim 3 wherein the tracking of specimens includes the process of using the specimen information stored on the RFID Specimen Transport Pucks and RFID Readers to locate said specimens while in said pucks throughout the laboratory.

19. The method of claim 3 wherein the tracking of specimens includes the process of using the specimen information stored on the RFID Specimen Transport Pucks and said RFID Readers to receive specimen identifying information at lab handoff locations into a software tracking system with date and time stamps to locate specimens throughout the laboratory.

20. The method of claim 1 wherein the receiving of specimen identifying information of specimens into a database information system occurs from RFID Readers located beneath a conveyor while RFID Specimen Transport Pucks carrying specimens pass over the readers and are sorted based on specimen information stored in the RFID Puck from the conveyor into sort trays and/or sleeves.

* * * * *